US012746136B2

(12) United States Patent
Marrey et al.

(10) Patent No.: US 12,746,136 B2
(45) Date of Patent: Sep. 29, 2026

(54) IMPLANTABLE EXPANDABLE STRUCTURES FOR TREATING SMALL VESSELS

(71) Applicant: Covidien LP, Mansfield, MA (US)

(72) Inventors: Ramesh V. Marrey, Mission Viejo, CA (US); David C. Majercak, Bloomington, IN (US)

(73) Assignee: Covidien LP, Mansfield, MA (US)

(*) Notice: Subject to any disclaimer, the term of this patent is extended or adjusted under 35 U.S.C. 154(b) by 370 days.

(21) Appl. No.: 18/600,140

(22) Filed: Mar. 8, 2024

(65) Prior Publication Data

US 2024/0277500 A1 Aug. 22, 2024

Related U.S. Application Data

(60) Provisional application No. 63/485,702, filed on Feb. 17, 2023.

(51) Int. Cl.
*A61F 2/915* (2013.01)

(52) U.S. Cl.
CPC .... *A61F 2/915* (2013.01); *A61F 2002/91525* (2013.01); *A61F 2002/91558* (2013.01); *A61F 2002/91583* (2013.01)

(58) Field of Classification Search
CPC .. A61F 2002/91558; A61F 2002/91583; A61F 2002/91525; A61F 2002/91541; A61F 2250/0036
See application file for complete search history.

(56) References Cited

U.S. PATENT DOCUMENTS

| | | | | |
|---|---|---|---|---|
| 2001/0029397 | A1* | 10/2001 | Thompson | A61F 2/915 600/36 |
| 2007/0239263 | A1* | 10/2007 | Fliedner | A61F 2/915 623/1.22 |
| 2012/0123524 | A1 | 5/2012 | Girton et al. | |
| 2012/0226346 | A1 | 9/2012 | Boismier et al. | |
| 2013/0289702 | A1 | 10/2013 | Coghlan et al. | |
| 2016/0250046 | A1 | 9/2016 | Denison et al. | |
| 2018/0028338 | A1 | 2/2018 | Rangwala et al. | |

* cited by examiner

*Primary Examiner* — Javier G Blanco

(74) *Attorney, Agent, or Firm* — Fortem IP LLP

(57) ABSTRACT

Expandable structures for treating blood vessels are disclosed herein. According to some embodiments, the present technology includes a stent, comprising a plurality of struts connected to one another at a plurality of apices, wherein the struts are arranged in a plurality of bands, each band extending around a circumference of the stent. Within a given band, the struts may be connected end-to-end, and may comprise a repeating series of circumferentially adjacent struts. The series may comprise a pair of thin struts each having a first width, a pair of thick struts each having a second width, and an intermediate strut between the thick and thin struts and that has a third width that is greater than the first width and less than the second width.

20 Claims, 5 Drawing Sheets

FIG. 1B

IMPLANTABLE EXPANDABLE STRUCTURES FOR TREATING SMALL VESSELS

CROSS-REFERENCE TO RELATED APPLICATIONS

This application claims the benefit of and priority to U.S. Provisional Patent Application Ser. No. 63/485,702 filed Feb. 17, 2023, the entire disclosure of which is incorporated by reference herein.

TECHNICAL FIELD

The present technology relates to implantable expandable structures for treating small vessels. In particular, the present technology relates to implantable expandable structures for treating vascular conditions.

BACKGROUND

Generally, stents are used as an alternative to surgery to obtain and maintain the patency of a variety of body passageways, while maintaining the integrity of the passageway. The environments of human vasculature and body passageways are characterized by varied, dynamic, and mobile anatomy. Vessels vary from simple to complex shapes, can be uniform in diameter or change abruptly or gradually from one diameter to another, and are subjected to a range of internal forces exerted by blood or air pressure, and external forces exerted by an assortment of anatomical structures surrounding and adjacent to these body passageways. Stents are typically designed to provide scaffolding and structural support within the affected vessel segment while maintaining a degree of flexibility required by particular indications of use.

Neurovascular conditions can be particularly difficult to treat with stents as the blood vessels are small and tortuous. Current stent designs have difficulty approximating the vessel wall along portions of the neurovasculature that are curved, twisted, or forked. Current designs generally suffer from crimping or kinking when positioned in such tortuous vessels. This can be problematic for several reasons. When using a stent to treat intracranial atherosclerotic disease (ICAD), for example, inconsistent or weak wall apposition prevents the stent from sufficiently opening a stenosis and improving intracranial flow. Stents are also used to bridge wide-necked aneurysms to prevent coils within the aneurysm from protruding through the aneurysm neck into the parent vessel. If the parent vessel is curved, twisted, or forked, current stent designs have difficulty achieving consistent wall apposition across the neck, thereby allowing the coils to protrude and/or allowing blood to flow into the aneurysm.

Accordingly, there exists a need for improved stents for treating neurovascular conditions, such as ICAD and hemorrhagic stroke.

SUMMARY

The present technology is directed to expandable structures configured to be positioned in a blood vessel lumen, such as within the neurovasculature, to treat one or more conditions. As discussed in greater detail herein, the expandable structure of the present technology comprises a tubular member formed of a plurality of interconnected struts arranged in a geometry that enable delivery of the expandable structure in a low-profile state with enhanced pushability. The strut geometry also allows the expandable structure to conform to the vessel wall and maintain wall apposition when implanted. The subject technology is illustrated, for example, according to various aspects described below, including with reference to FIGS. 1A-4. Various examples of aspects of the subject technology are described as numbered clauses (1, 2, 3, etc.) for convenience. These are provided as examples and do not limit the subject technology.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Many embodiments of the subject technology are directed to expandable structures configured to be implanted in a blood vessel lumen to treat one or more vascular conditions. The expandable structures can comprise a plurality of interconnected struts that together define a tubular sidewall. As detailed below, the size and arrangement of the struts enable the expandable structures of the present technology to maintain apposition with the vessel wall when positioned around tight corners or bends and avoids or eliminates kinking. Moreover, the expandable structures of the present technology have a strut geometry that provides improved column strength when the expandable structure is in a compressed state for delivery, thereby providing improved pushability.

Figure 1A:
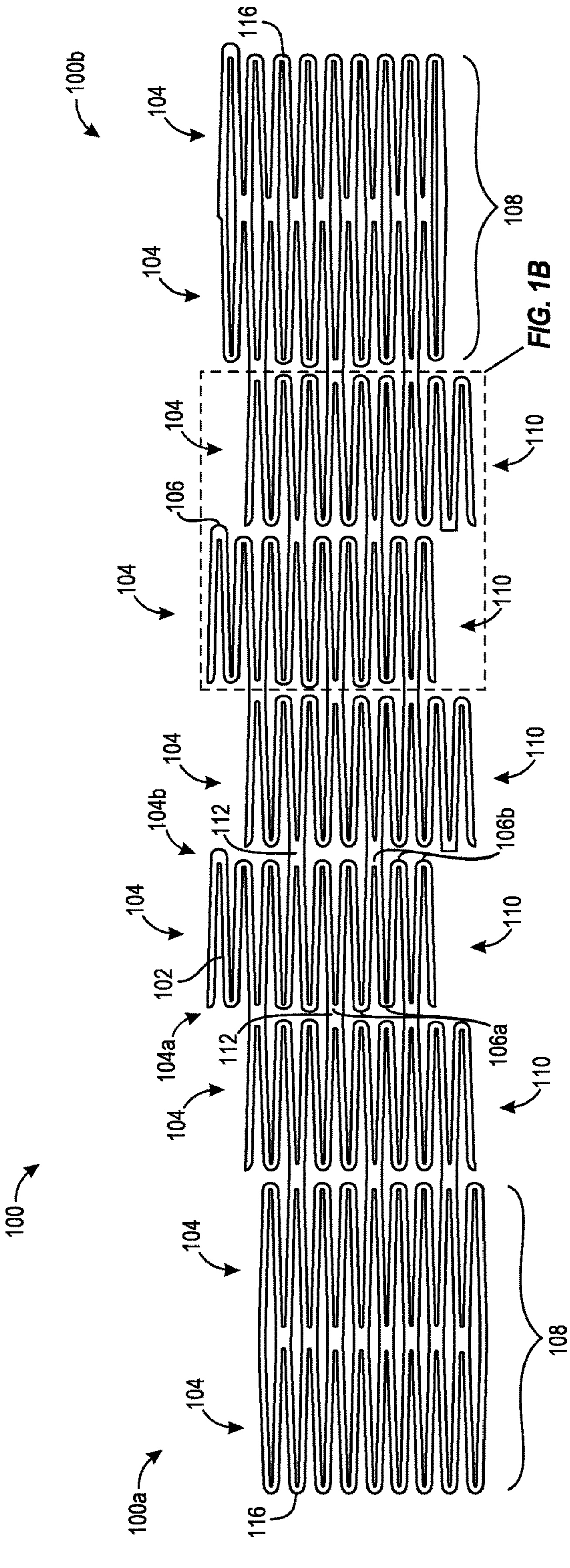
FIG. 1A is an unwrapped schematic view of an expandable structure configured in accordance with several embodiments of the present technology.
Figure 1B:
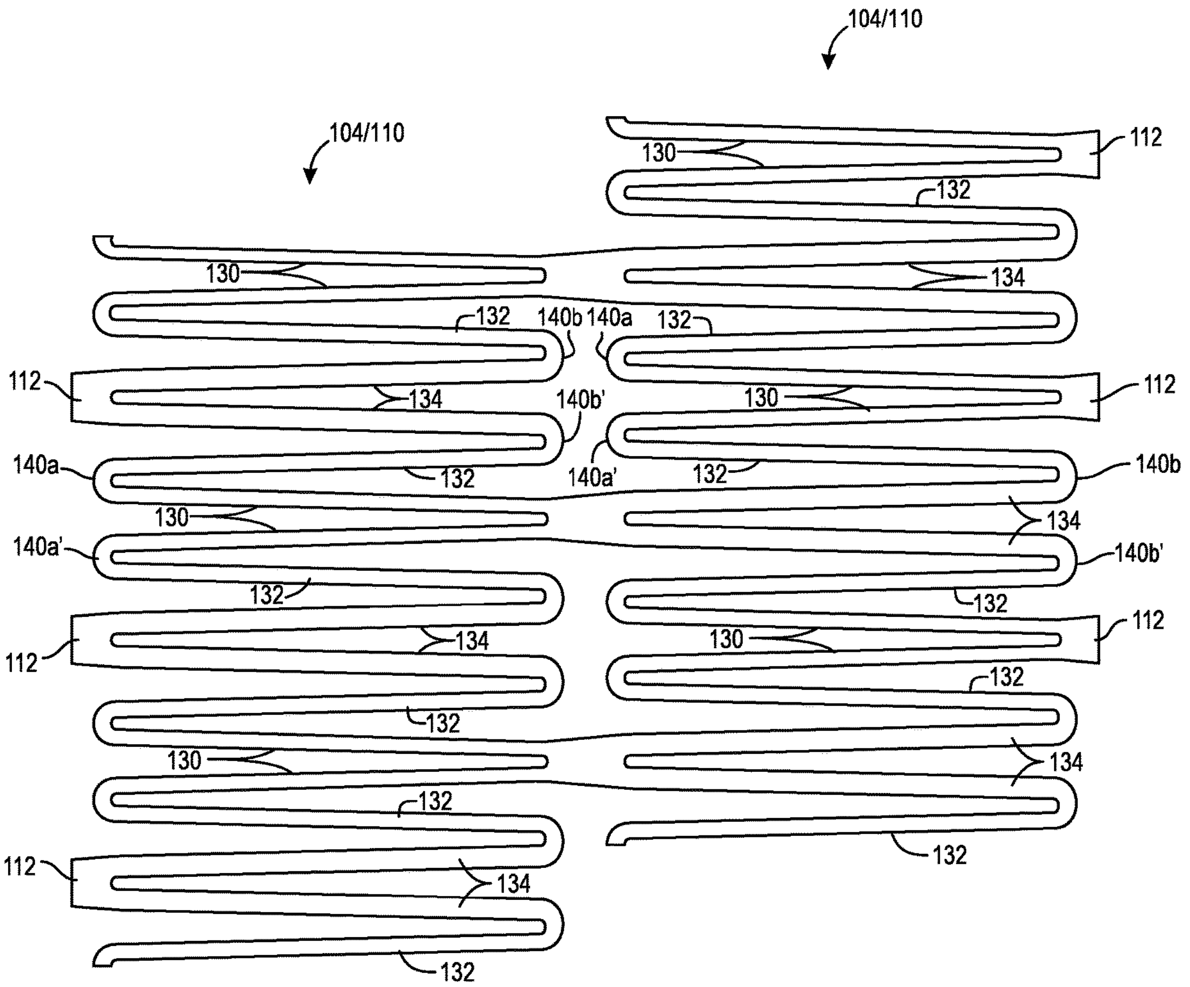
FIG. 1B is an enlarged view of a portion of the expandable structure shown in FIG. 1A.
Figure 2A:
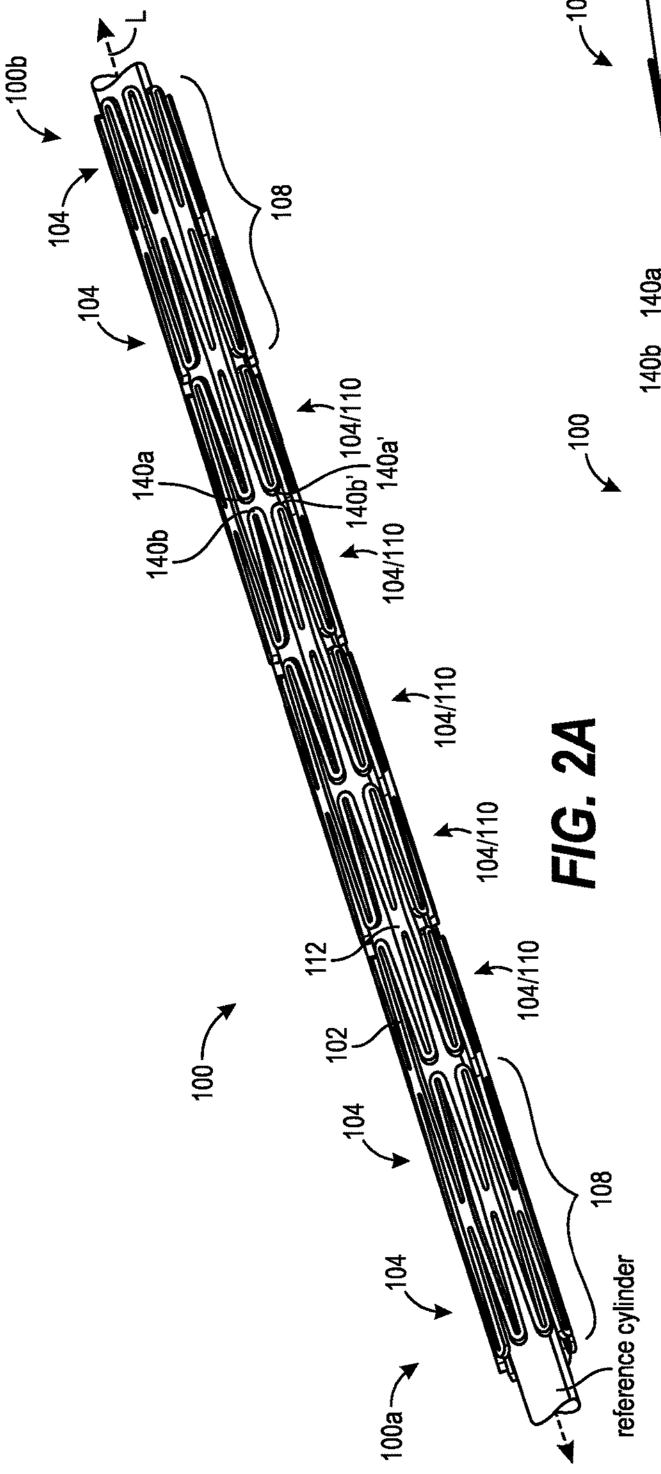
FIG. 2A is a perspective view of the expandable structure of FIG. 1A in tubular form, shown in a compressed configuration in accordance with several embodiments of the present technology. A reference cylinder is drawn through the lumen of the expandable structure to better illustrate and distinguish the near struts from the far (now covered) struts.
Figure 2B:
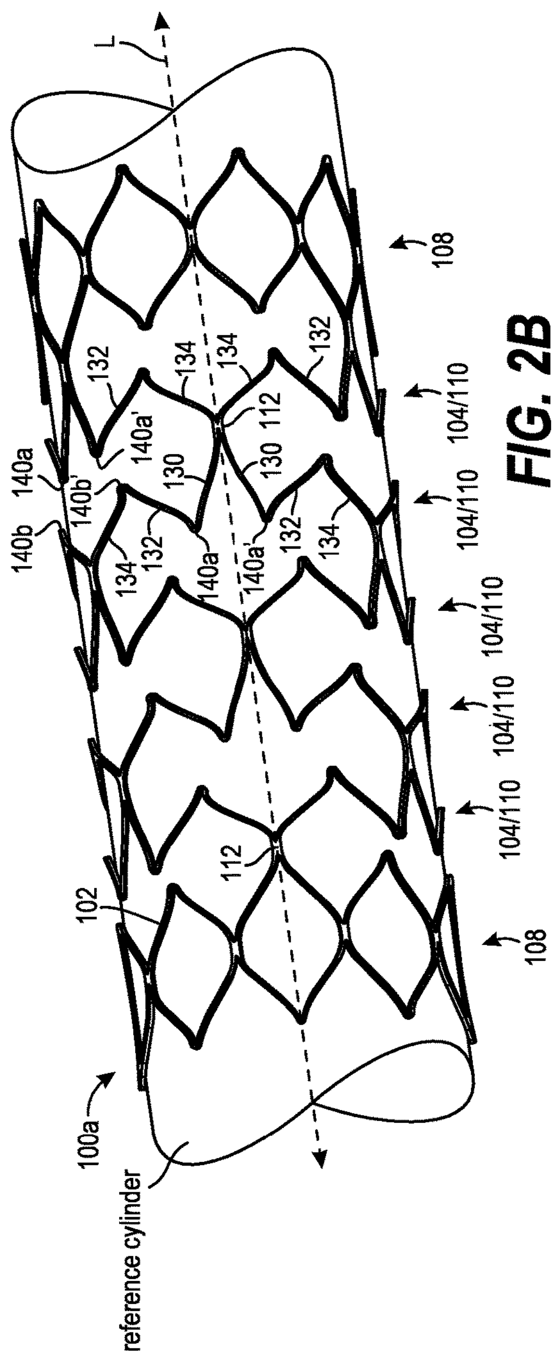
FIG. 2B is a perspective view of the expandable structure of FIG. 1A in tubular form, shown in an expanded configuration in accordance with several embodiments of the present technology. A reference cylinder is drawn through the lumen of the expandable structure to better illustrate and distinguish the near struts from the far (now covered) struts.

FIG. 1A illustrates an expandable structure 100, shown longitudinally split and laid flat, and FIG. 1B shows an enlarged portion of FIG. 1A. It will be appreciated that the expandable structure 100 is intended to be used in a tubular configuration (as shown in FIGS. 2A and 2B) and the laid flat views shown in FIGS. 1A and 1B are provided herein to better illustrate a strut geometry. The expandable structure

100 may be formed, for example, by laser cutting a tube, laser cutting a flat sheet then rolling it up and fusing the edges, by vapor deposition techniques, or combinations thereof. The expandable structure 100 can be formed using known flexible materials such as nitinol, stainless steel, cobalt-chromium alloys, Elgiloy, magnesium alloys, tungsten, tantalum, platinum, or combinations thereof.

The expandable structure 100 can comprise a tubular member having a first end portion 100*a*, a second end portion 100*b*, and a longitudinal axis L (labeled in FIGS. 2A and 2B) extending therebetween. The tubular member can have a compressed configuration (see FIG. 2A) for delivery through a catheter to a treatment site within a blood vessel lumen and an expanded configuration (see FIG. 2B) for implantation in a blood vessel lumen. The expandable structure 100 can comprise a plurality of struts 102 arranged within a plurality of bands 104, each band 104 extending around a circumference of the expandable structure 100 when the expandable structure 100 forms a tubular shape. Each of the struts 102 connect to another strut 102 at an apex 106 (only a few labeled). Each of the bands 104 can have a first side 104*a* that is closer to the first end portion 100*a* along the longitudinal axis L and a second side 104*b* that is closer to the second end portion 100*b* along the longitudinal axis L.

As used herein, structures that are "longitudinally adjacent" are immediately adjacent one another along the longitudinal axis L of the expandable structure 100. For example, each of the bands 104 is longitudinally adjacent one or two other bands 104. Likewise, structures that are "circumferentially adjacent" are immediately adjacent one another along a circumference of the expandable structure 100. For example, within a given band 104, each strut 102 is circumferentially adjacent two other struts (as described below).

In some embodiments, the bands 104 can comprise end bands 108 disposed at the first and second end portions 100*a*, 100*b*, respectively, and intermediate bands 110 disposed between the end bands 108 along the longitudinal axis L of the expandable structure 100. While each of the intermediate bands 110 comprises a single band 104, each of the end bands 108 can comprise one or more bands 104. In FIG. 1A, the end bands 108 comprise two bands 104. In other embodiments, the end bands 108 may comprise a single band 104, or may comprise more than two bands. While the expandable structure 100 shown in FIG. 1A comprises five intermediate bands 110, in some embodiments the expandable structure may comprise more or fewer than five intermediate bands 110. As described in greater detail below, the strut geometry of the end bands 108 can be different than the strut geometry of the intermediate bands 110 to impart different structural properties to different portions of the expandable structure 100.

Within some or all of the bands 104, the struts 102 may be connected end-to-end to form alternating "V's" such that the struts 102 are circumferentially disposed in a zigzag or "Z" pattern. Circumferentially adjacent struts 102 within a given band 104 may connect to one another at apices 106, and the bands 104 may have first apices 106*a* that point towards the first end portion 100*a* of the expandable structure 100 and second apices 106*b* that point towards the second end portion 100*b* of the expandable structure 100. As such, the first side 104*a* of each band 104 can be defined by a plurality of first apices 106*a* and the second side 104*b* of each band 104 can be defined by a plurality of second apices 106*b*.

Longitudinally adjacent bands 104 may be connected to one another via bridges 112. In particular, each bridge 112 connects a first apex 106*a* on one band 104 with a second apex 106*b* on a longitudinally adjacent band 104. As a result, each bridge 112 occurs at the intersection of four struts 102 (two from one band 104 and two from the longitudinally adjacent band 104). For each intermediate band 110, at least some, but not all, of the individual first apices 106*a* form bridges 112 with one of the second apices 106*b* of a longitudinally adjacent band 104 and at least some, but not all, of the individual second apices 106*b* form bridges 112 with one of the first apices 106*b* of another longitudinally adjacent band. The first and second apices 106*a*, 106*b* of an intermediate band 110 that do not form part of a bridge 112 are referred to herein as "free" apices. Accordingly, each of the first side 104*a* and the second side 104*b* of each intermediate band 110 includes one or more bridges 112 (e.g., connected apices 106) and one or more free apices 106.

In some embodiments, some or all of the intermediate bands 110 can have a repeating pattern of two consecutive free first apices 106*a* followed by a bridge 112 (along the circumference of the expandable structure 100), and two consecutive free second apices 106*b* followed by a bridge 112. In other embodiments, some or all of the intermediate bands 110 may have a different number or sequence of free apices and bridges.

When the expandable structure 100 is in the compressed configuration, as shown in FIG. 2A, the individual free first apices 106*a* of the intermediate bands 110 may be circumferentially aligned with a corresponding one of the free second apices 106*b* of a longitudinally adjacent band 104. As used herein, "opposing free apices" refers to a pair of free first and second apices 106*a*, 106*b* in longitudinally adjacent bands 104 that are circumferentially aligned when the expandable structure 100 is in the compressed configuration. The opposing free apices thus point towards one another in the compressed configuration and are separated longitudinally by a small gap. The opposing free apices can beneficially provide increased axial stiffness and pushability for delivery to the treatment site.

Figure 1C:
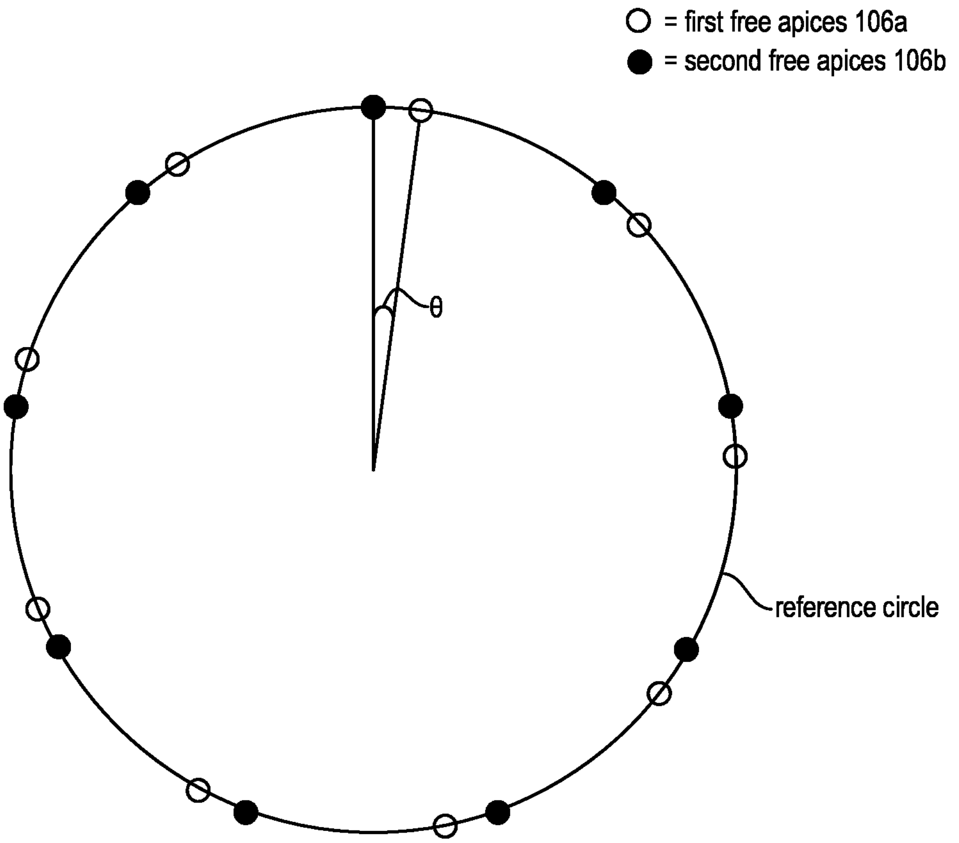
FIG. 1C schematically depicts measurement of circumferential alignment of opposing free apices of an expandable structure configured in accordance with several embodiments of the present technology.

As used herein, structures that are "circumferentially aligned," such as opposing free apices 106*a*, 106*b* when the expandable structure 100 is in the compressed configuration, are disposed at the same or substantially the same location along the circumference of the expandable structure 100 such that a line joining such structures is parallel or substantially parallel to a longitudinal axis of the expandable structure 100. With reference to FIG. 1C, circumferential alignment of the opposing free apices 106*a*, 106*b* can be measured by the angle θ, where θ is defined by the angle subtended by an arc connecting two opposing strut apices 106*a*, 106*b* (when viewed in the same cross-sectional plane, as shown in FIG. 1C) to a point on the central longitudinal axis of the expandable structure 100. In some embodiments, the angle θ is between 0 and 8 degrees. In certain embodiments, the angle θ is between 0 and 4 degrees. According to several embodiments, the angle θ is between 0 and 2 degrees, or between 0 and 1 degree. In certain embodiments, the angle θ is 0 degrees. FIG. 1C shows a phase shift in which all of the opposing apices 106*a*, 106*b* are circumferentially misaligned by the same amount. In certain cases, however, one or more of the opposing apices 106*a*, 106*b* may be misaligned by different amounts.

As previously mentioned, the end bands 108 can comprise a geometry and/or structure that is different than the intermediate bands 110. For example, as shown in FIG. 1A, the end bands 108 can comprise two or more bands 104 in which all of the first and second apices 106*a*, 106*b* between adjacent bands are joined by bridges 112. Said another way, for a given end band 108, the longitudinally adjacent bands 104 do not have any free apices between them. Such a construction may be beneficial for providing greater stability and anchoring at the ends of the expandable structure 100, and for providing greater visibility under fluoroscopy. Each of the end bands 108 can comprise free terminal apices 116, and the sides of the end bands 108 that connect to an intermediate band 110 have one or more free apices.

Figure 3:
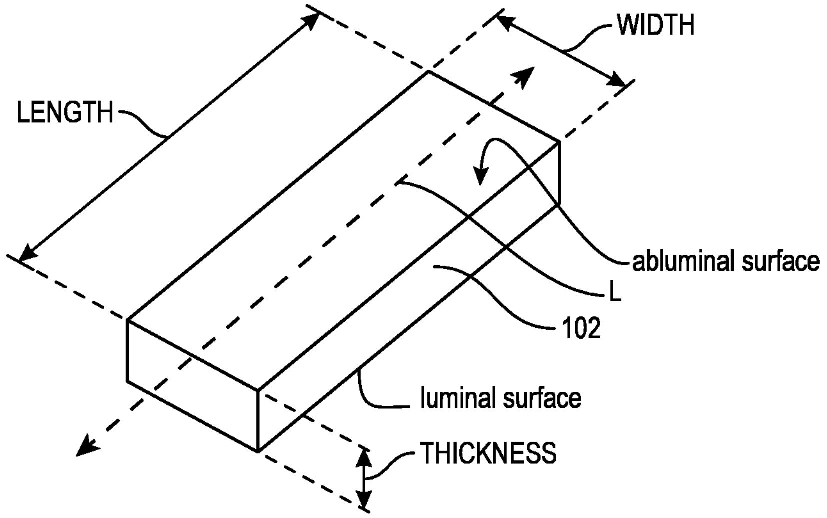
FIG. 3 shows a perspective view of a strut, according to several embodiments of the present technology.
Figure 4:
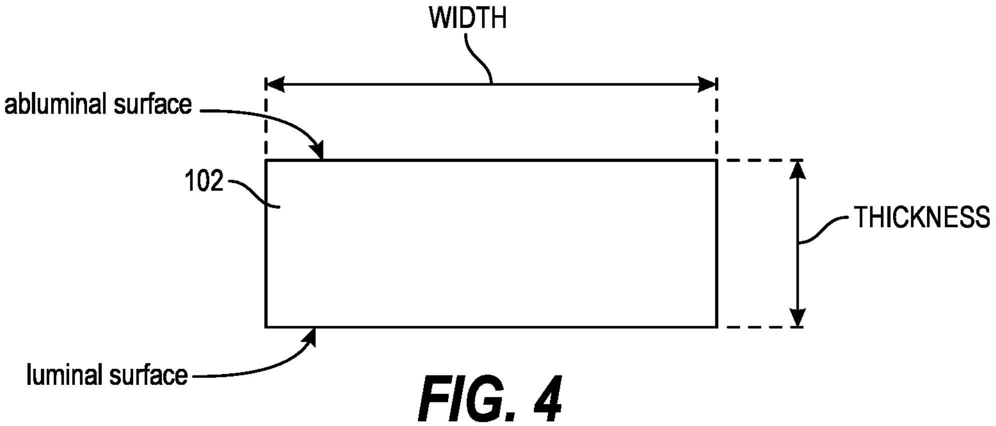
FIG. 4 shows a cross-sectional view of a strut, according to several embodiments of the present technology.

With reference to FIGS. 3 and 4, each of the struts 102 has a length measured along a longitudinal axis L of the respective strut 102 between its ends (e.g., between first and second apices 106*a*, 106*b*). Each of the struts 102 also has a thickness measured between the abluminal and luminal surfaces of the struts 102 (i.e., as a dimension that is orthogonal to a central axis when the expandable structure 100 is considered in a tubular shape or as a dimension that is orthogonal to a plane of the expandable structure 100 when represented as laid-flat). Each of the struts 102 also has a width measured as a distance that is orthogonal to the longitudinal and radial dimensions of the respective strut 102.

In some embodiments, the widths of the struts 102 within a given intermediate band 110 can vary from strut to strut. For example, with reference to FIG. 1B, in some embodiments the intermediate bands 110 comprise one or more narrow struts 130, one or more intermediate struts 132, and one or more wide struts 134. The individual intermediate struts 132 can have a width that is greater than the widths of the individual narrow struts 130, and the individual wide struts 134 can have a width that is greater than the widths of the individual intermediate struts 132. In some embodiments, one, some, or all of the intermediate bands 110 include struts 102 of only two different widths (e.g., narrower struts and wider struts).

Struts having different widths may be distributed within a given intermediate band 110 and across adjacent intermediate bands 110 in an arrangement that allows longitudinally adjacent free apices to be circumferentially aligned when the expandable structure 100 is in the compressed configuration but forces those free apices to be circumferentially offset when the expandable structure 100 is in the expanded configuration. Having the apices aligned in the compressed configuration advantageously provides increased axial stiffness and pushability during delivery, while the offset in the expanded configuration provides increased stent conformability and wall apposition by reducing the likelihood of apices colliding when the expandable structure 100 is forced around a tight curve.

In some embodiments the struts 102 within some or all of the intermediate bands 110 may be arranged according to width in a pattern that repeats around the circumference of the intermediate band 110. For example, as shown in FIG. 1B, some or all of the intermediate bands 110 can include the following repeating pattern: narrow strut 130—narrow strut 130—intermediate strut 132—wide strut 134—wide strut 134—intermediate strut 132. As such, the struts 102 are arranged within the intermediate band 110 such that, within a single sequence of the foregoing pattern, each free apex has a different combination of strut widths or a different relative orientation of struts of certain widths. To illustrate, examples of the differing apices have been labeled in FIG. 1B and will now be described. Each intermediate band 110 can have (a) a first free apex 140*a* joining a narrow strut 130 and an intermediate strut 132, where the narrow strut 130 is positioned below (clockwise of) the first free apex 140*a* and the intermediate strut 132 is positioned above (counterclockwise of) the first free apex 140*a*; (b) another first free apex 140*a*', circumferentially adjacent and on the same side of the band 110 as first free apex 140, the first free apex 140*a*' joining a narrow strut 130 and an intermediate strut 132, this time with the intermediate strut 132 positioned below (clockwise of) the first free apex 140*a*' and the narrow strut 130 positioned above (counterclockwise of) the first free apex 140*a*'; (c) a second free apex 140*b* joining an intermediate strut 132 and a wide strut 134, where the intermediate strut 132 is positioned above (counterclockwise of) the second free apex 140*b* and the wide strut 134 is positioned below (clockwise of) the second free apex 140*b*; and (d) another second free apex 140*b*' joining an intermediate strut 132 and a wide strut 134, where the wide strut 134 is positioned above (counterclockwise of) the second free apex 140*b*' and the intermediate strut 132 is positioned below (clockwise of) the second free apex 140*b*'.

As the expandable structure 100 moves towards an expanded configuration and a diameter of the bands 104 increases (such that an arc length between circumferentially adjacent bridges 112 increases), the free apices between circumferentially adjacent bridges 112 will move circumferentially away from one another to a degree determined by the widths of the struts forming the free apices and their polarity. For example, when the expandable structure 100 is in the expanded configuration, the first free apices 140*a*, 140*a*' will be separated by an arc length that is less than the arc length of separation between the second free apices 140*b*, 140*b*'. This is because the struts 102 forming the 'V' between the first free apices 140*a*, 140*a*' are narrow struts 130 (e.g., lower bending stiffness and more compliant) while the struts 102 forming the 'V' between the second free apices 140*b*, 140*b*' are wide struts 134 (e.g., higher bending stiffness and less compliant). As a result, the first free apices 140*a*, 140*a*' move circumferentially away from one another to a lesser extent than the second free apices 140*b*, 140*b*' when the expandable structure 100 expands.

Adjacent intermediate bands 110 can comprise the same pattern of struts 102, but the pattern can be shifted circumferentially so that the second free apices 140*b*, 140*b*' of one intermediate band 100 are circumferentially aligned with the first free apices 104*a*, 140*a*', respectively, of the longitudinally adjacent band 110. As a result, a second free apex 140*b*, having a polarity in which the wider of the two connected struts is below (clockwise) the second free apex 140*b*, is circumferentially aligned (in the compressed configuration) with a first free apex 140*a* having a polarity in which the wider of the two struts is above (counterclockwise) the first free apex 140*a*. Likewise, another second free apex 140*b*', having a polarity in which the wider of the two connected struts is above (counterclockwise) the second free apex 140*b*', is circumferentially aligned (in the compressed configuration) with another first free apex 140*a*' having a polarity in which the wider of the two struts is below (clockwise) the first free apex 140*a*'. This asymmetry of strut widths amongst opposing free apices enables non-uniform spacing of the free apices when the expandable structure 100 is in the expanded configuration such that the free apices are no longer circumferentially aligned.

The expandable structures of the present technology can be deployed in any blood vessel. In some embodiments, the expandable structures are configured to be deployed in an intracranial blood vessel. For example, the expandable structures of the present technology can be configured to treat acute or symptomatic ICAD. In such cases, the expandable structure can be configured to be deployed in the blood vessel to open the ICAD stenosis and allow for intracranial blood flow. The expandable structures of the present technology may also be used for stent-assisted coiling to treat hemorrhagic stroke. In such embodiments, the expandable structures can be configured to be positioned across the neck of a wide-necked aneurysm to prevent protrusion of already-delivered coil into the parent vessel. Other neurovascular and non-neurovascular treatments are also possible.

The follow clauses describe embodiment of the present technology:

A treatment device comprising:

a tubular member having a first end, a second end, and a longitudinal axis extending therebetween, wherein the tubular member has a compressed configuration for delivery through a catheter and an expanded configuration in which the tubular member is configured to be implanted in a blood vessel lumen, and wherein the tubular member comprises a plurality of struts arranged in a plurality of bands, each band extending circumferentially about the tubular member, and wherein, within each of the bands, circumferentially adjacent struts are coupled at their respective ends at an apex such that each band includes a plurality of apices, and wherein the plurality of apices of each band includes:

connector apices, each of which is connected to a corresponding connector apex of a longitudinally adjacent one of the bands, and free apices that do not connect to one of the longitudinally adjacent bands, wherein the free apices include first free apices disposed at a first longitudinal end of a corresponding band and second free apices disposed at a second longitudinal end of a corresponding band, wherein each of the plurality of struts has a width measured orthogonal to longitudinal and radial dimensions of the respective strut, and wherein the bands include a first band and a second band longitudinally adjacent to the first band, wherein:

the first band includes a first pair of struts connected by a second free apex, wherein one strut of the first pair of struts is wider than the other strut of the first pair of struts, and wherein the one strut is positioned clockwise of the second free apex along a circumference of the tubular member, the second band includes a second pair of struts connected by a first free apex, wherein one strut of the second pair of struts is wider than the other strut of the second pair of struts, and wherein the one strut is positioned counterclockwise of the first free apex along the circumference of the tubular member, wherein, when the tubular member is in the compressed configuration, the first free apex of the first band is circumferentially aligned with the second free apex of the second band, and wherein, when the tubular member is in the expanded configuration, the first free apex of is circumferentially offset from the second free apex.

The treatment device of Clause 1, wherein the first and second free apices are aligned at a circumferential location when the tubular member is in the compressed configuration, and wherein, when the tubular member is in the expanded configuration, the first free apex of the first band is circumferentially offset from the second free apex of the second band such that the first free apex is positioned counterclockwise of the circumferential location and the second free apex is positioned counterclockwise of the circumferential location.

The treatment device of Clause 1 or Clause 2, wherein the one strut of the second pair of struts has the same width as the other strut of the first pair of struts.

The treatment device of any one of the previous Clauses, wherein the one strut of the first pair of struts is wider than the other strut of the second pair of struts.

The treatment device of any one of the previous Clauses, wherein:

the first band includes a third pair of struts connected by a fourth free apex, wherein one strut of the third pair of struts is wider than the other strut of the third pair of struts, and wherein the one strut of the third pair of struts is positioned counterclockwise of the fourth free apex along a circumference of the tubular member, the second band includes a fourth pair of struts connected by a third free apex, wherein one strut of the fourth pair of struts is wider than the other strut of the fourth pair of struts, and wherein the one strut of the fourth pair of struts is positioned clockwise of the third free apex along the circumference of the tubular member.

The treatment device of Clause 5, wherein the second and fourth free apices are circumferentially adjacent along the circumference of the tubular member and the first and third free apices are circumferentially adjacent.

The treatment device of Clause 5 or Clause 6, wherein, when the tubular member is in the compressed configuration, the fourth free apex of the first band is circumferentially aligned with the third free apex of the second band.

The treatment device of any one of Clauses 5 to 7, wherein, when the tubular member is in the expanded configuration, the first and third apices are separated by an arc length that is less than an arc length between the second and fourth apices.

The treatment device of any one of Clauses 5 to 8, wherein a width of the one strut of the first pair of struts is the same as a width of the one strut of the third pair of struts.

The treatment device of any one of Clauses 5 to 9, wherein a width of the one strut of the second pair of struts is the same as a width of the one strut of the fourth pair of struts.

The treatment device of any one of Clauses 1 to 10, wherein the struts of the first band include narrow struts, intermediate struts, and wide struts, wherein the wide struts have a width that is greater than a width of the intermediate struts, and the intermediate struts have a width that is greater than a width of the narrow struts.

The treatment device of Clause 11, wherein the one strut of the first pair of struts is a wide strut.

The treatment device of Clause 11 or Clause 12, wherein the other strut of the first pair of struts is an intermediate strut.

The treatment device of any one of Clauses 11 to 13, wherein the one strut of the second pair of struts is an intermediate strut.

The treatment device of any one of Clauses 11 to 13, wherein the other strut of the second pair of struts is a narrow strut.

The treatment device of any one of Clauses 11 to 13, wherein the one strut of the third pair of struts is a wide strut.

The treatment device of any one of Clauses 11 to 13, wherein the other strut of the third pair of struts is an intermediate strut.

The treatment device of any one of Clauses 11 to 13, wherein the one strut of the fourth pair of struts is an intermediate strut.

The treatment device of any one of Clauses 11 to 13, wherein the other strut of the fourth pair of struts is a narrow strut.

A treatment device comprising:

a tubular member having a first end, a second end, and a longitudinal axis extending therebetween, wherein the tubular member has a compressed configuration for delivery through a catheter and an expanded configuration in which the tubular member is configured to be implanted in a blood vessel lumen, and wherein the tubular member comprises a plurality of struts arranged in a plurality of bands, each band extending circumferentially about the tubular member, and wherein, within each of the bands, circumferentially adjacent struts are coupled at their respective ends at an apex such that each band includes a plurality of apices, and wherein the plurality of apices of each band includes:

connector apices, each of which is connected to a corresponding apex of a longitudinally adjacent one of the bands, and free apices that do not connect to one of the longitudinally adjacent bands, wherein the free apices include first free apices disposed at a first longitudinal end of a corresponding band and second free apices disposed at a second longitudinal end of a corresponding band, wherein each of the plurality of struts has a width measured orthogonal to longitudinal and radial dimensions of the tubular member, and wherein, when the tubular member is in the compressed configuration, the first free apices of a first one of the bands are circumferentially aligned with the second free apices of a second one of the bands that is longitudinally adjacent the first one of the bands, wherein, for each aligned pair of first free apices and second free apices:

the first free apices connect a narrower one of the struts within the first one of the bands to a wider one of the struts within the first one of the bands, the narrower one of the struts having a width that is less than a width of the wider one of the struts, and wherein the narrower one of the struts is disposed clockwise of the wider one of the struts about a circumference of the tubular member, the second free apices connect a narrower one of the struts within the second one of the bands to a wider one of the struts within the second one of the bands, the narrower one of the struts in the second one of the bands having a width that is less than a width of the wider one of the struts in the second one of the bands, and wherein the narrower one of the struts in the second one of the bands is disposed counter-clockwise of the wider one of the struts in the second one of the bands about a circumference of the tubular member, wherein, when the tubular member is in the expanded configuration, the first free apices of the first one of the bands are circumferentially offset from the second free apices of the second one of the bands.

A stent, comprising:

a plurality of struts connected to one another at a plurality of apices, wherein the struts are arranged in a plurality of bands, each band extending around a circumference of the stent, wherein, within a given band, the struts are connected end-to-end, and wherein within a given band, the struts comprise a repeating series of circumferentially adjacent struts, the series comprising: a pair of thin struts each having a first width, a pair of thick struts each having a second width, and an intermediate strut between the thick and thin struts and that has a third width that is greater than the first width and less than the second width.

CONCLUSION

Although many of the embodiments are described above with respect to systems, devices, and methods for treating neurovascular conditions, the technology is applicable to other applications and/or other approaches, such as other vascular applications, including coronary, peripheral vascular, and others. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-4.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A treatment device comprising:

a tubular member having a first end, a second end, and a longitudinal axis extending therebetween, wherein the tubular member has a compressed configuration for delivery through a catheter and an expanded configuration in which the tubular member is configured to be implanted in a blood vessel lumen, and wherein the tubular member comprises a plurality of struts arranged in a plurality of bands, each band extending circumferentially about the tubular member, and wherein, within each of the bands, circumferentially adjacent struts are coupled at their respective ends at an apex such that each band includes a plurality of apices, and wherein the plurality of apices of each band includes:

connector apices, each of which is connected to a corresponding connector apex of a longitudinally adjacent one of the bands, and free apices that do not connect to one of the longitudinally adjacent bands, wherein the free apices include first free apices disposed at a first longitudinal end of a corresponding band and second free apices disposed at a second longitudinal end of a corresponding band, wherein each of the plurality of struts has a width measured orthogonal to longitudinal and radial dimensions of the respective strut, and wherein the bands include a first band and a second band longitudinally adjacent to the first band, wherein:

the first band includes a first pair of struts connected by a second free apex, wherein one strut of the first pair of struts is wider than the other strut of the first pair of struts, and wherein the one strut is positioned clockwise of the second free apex along a circumference of the tubular member, the second band includes a second pair of struts connected by a first free apex, wherein one strut of the second pair of struts is wider than the other strut of the second pair of struts, and wherein the one strut of the second pair of struts is positioned counterclockwise of the first free apex along the circumference of the tubular member, wherein, when the tubular member is in the compressed configuration, the first free apex of the first band is circumferentially aligned with the second free apex of the second band, and wherein, when the tubular member is in the expanded configuration, the first free apex of the first band is circumferentially offset from the second free apex of the second band.

2. The treatment device of claim 1, wherein the first and second free apices are aligned at a circumferential location when the tubular member is in the compressed configuration, and wherein, when the tubular member is in the expanded configuration, the first free apex of the first band is circumferentially offset from the second free apex of the second band such that the first free apex is positioned counterclockwise of the circumferential location and the second free apex is positioned counterclockwise of the circumferential location.

3. The treatment device of claim 1, wherein the one strut of the second pair of struts has the same width as the other strut of the first pair of struts.

4. The treatment device of claim 1, wherein the one strut of the first pair of struts is wider than the other strut of the second pair of struts.

5. The treatment device of claim 1, wherein:

the first band includes a third pair of struts connected by a fourth free apex, wherein one strut of the third pair of struts is wider than the other strut of the third pair of struts, and wherein the one strut of the third pair of struts is positioned counterclockwise of the fourth free apex along a circumference of the tubular member, the second band includes a fourth pair of struts connected by a third free apex, wherein one strut of the fourth pair of struts is wider than the other strut of the fourth pair of struts, and wherein the one strut of the fourth pair of struts is positioned clockwise of the third free apex along the circumference of the tubular member.

6. The treatment device of claim 5, wherein the second and fourth free apices are circumferentially adjacent along the circumference of the tubular member and the first and third free apices are circumferentially adjacent.

7. The treatment device of claim 5, wherein, when the tubular member is in the compressed configuration, the fourth free apex of the first band is circumferentially aligned with the third free apex of the second band.

8. The treatment device of claim 5, wherein, when the tubular member is in the expanded configuration, the first and third apices are separated by an arc length that is less than an arc length between the second and fourth apices.

9. The treatment device of claim 5, wherein a width of the one strut of the first pair of struts is the same as a width of the one strut of the third pair of struts.

10. The treatment device of claim 5, wherein a width of the one strut of the second pair of struts is the same as a width of the one strut of the fourth pair of struts.

11. The treatment device of claim 1, wherein the struts of the first band include narrow struts, intermediate struts, and wide struts, wherein the wide struts have a width that is greater than a width of the intermediate struts, and the intermediate struts have a width that is greater than a width of the narrow struts.

12. The treatment device of claim 11, wherein the one strut of the first pair of struts is a wide strut.

13. The treatment device of claim 11, wherein the other strut of the first pair of struts is an intermediate strut.

14. The treatment device of claim 11, wherein the one strut of the second pair of struts is an intermediate strut.

15. The treatment device of claim 11, wherein the other strut of the second pair of struts is a narrow strut.

16. The treatment device of claim 11, wherein the one strut of the third pair of struts is a wide strut.

17. The treatment device of claim 11, wherein the other strut of the third pair of struts is an intermediate strut.

18. The treatment device of claim 11, wherein the one strut of the fourth pair of struts is an intermediate strut.

19. The treatment device of claim 11, wherein the other strut of the fourth pair of struts is a narrow strut.

20. A treatment device comprising:

a tubular member having a first end, a second end, and a longitudinal axis extending therebetween, wherein the tubular member has a compressed configuration for delivery through a catheter and an expanded configuration in which the tubular member is configured to be implanted in a blood vessel lumen, and wherein the tubular member comprises a plurality of struts arranged in a plurality of bands, each band extending circumferentially about the tubular member, and wherein, within each of the bands, circumferentially adjacent struts are coupled at their respective ends at an apex such that each band includes a plurality of apices, and wherein the plurality of apices of each band includes:

connector apices, each of which is connected to a corresponding connector apex of a longitudinally adjacent one of the bands, and free apices that do not connect to one of the longitudinally adjacent bands, wherein the free apices include first free apices disposed at a first longitudinal end of a corresponding band and second free apices disposed at a second longitudinal end of a corresponding band, wherein each of the plurality of struts has a width measured orthogonal to longitudinal and radial dimensions of the respective strut, and wherein, when the tubular member is in the compressed configuration, the first free apices of a first one of the bands are circumferentially aligned with the second free apices of a second one of the bands that is longitudinally adjacent the first one of the bands, wherein, for each aligned pair of first free apices and second free apices:

the first free apices connect a narrower one of the struts within the first one of the bands to a wider one of the struts within the first one of the bands, the narrower one of the struts having a width that is less than a width of the wider one of the struts, and wherein the narrower one of the struts is disposed clockwise of the wider one of the struts about a circumference of the tubular member, the second free apices connect a narrower one of the struts within the second one of the bands to a wider one of the struts within the second one of the bands, the narrower one of the struts in the second one of the bands having a width that is less than a width of the wider one of the struts in the second one of the bands, and wherein the narrower one of the struts in the second one of the bands is disposed counter-clockwise of the wider one of the struts in the second one of the bands about a circumference of the tubular member, wherein, when the tubular member is in the expanded configuration, the first free apices of the first one of the bands are circumferentially offset from the second free apices of the second one of the bands.

* * * * *